United States Patent
Suami

[11] 4,251,515
[45] Feb. 17, 1981

[54] NOVEL NITROSOUREA DERIVATIVES

[76] Inventor: Tetsuo Suami, 5-8, Nakamachi 3-chome, Musashino-shi, Tokyo, Japan

[21] Appl. No.: 30,510

[22] Filed: Apr. 16, 1979

[30] Foreign Application Priority Data

Apr. 15, 1978 [JP] Japan ................... 53-43800

[51] Int. Cl.³ ............. A61K 31/70; C07H 17/08
[52] U.S. Cl. ........................ 424/180; 536/22; 536/18; 536/53; 536/17 R
[58] Field of Search ......... 536/4, 22, 18, 53, 17 R; 424/180

[56] References Cited

U.S. PATENT DOCUMENTS

| | | | |
|---|---|---|---|
| 4,057,684 | 11/1977 | Kimura et al. | 536/18 |
| 4,086,415 | 4/1978 | Suami et al. | 536/22 |

*Primary Examiner*—Johnnie R. Brown
*Assistant Examiner*—Blondel Hazel
*Attorney, Agent, or Firm*—Haight, Rosfeld, Noble & Santa Maria

[57] ABSTRACT

Novel nitrosourea derivatives are provided which possess a high level of inhibitory activity against leukemia and tumors and other are therefore useful for pharmaceutical purposes. The compounds have the structure:

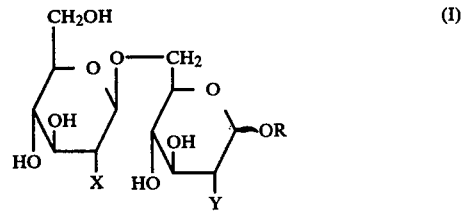

wherein one of X and Y represents a hydroxyl and another of them represents a group —NHCONNOCH$_2$CH$_2$Cl; R represents a hydrogen, alkyl or aryl; and ~ represents a single bond which may be in the α- or β-stereochemical configuration and are prepared by nitrosating a corresponding urea compound with a nitrosating agent in a manner known per se.

7 Claims, No Drawings

NOVEL NITROSOUREA DERIVATIVES

BACKGROUND OF THE INVENTION

This invention relates to novel nitrosourea derivatives which possess a high level of inhibitory activity against leukemia and other tumors and are therefore useful in therapeutic treatments of transplanted leukemic and tumor diseases. This invention further relates to a process for the preparation of such novel nitrosourea derivatives.

There are a variety of compounds which have been proposed as being effective for inhibiting leukemia and other tumors, of which one class is nitrosourea derivatives. Among the nitrosourea derivatives, there may be mentioned streptozotocin [N-(N'-methyl-N'-nitrosocarbamoyl)-D-glucosamine] and its derivatives such as methyl glucosaminides as being typical examples (refer to U.S. Pat. No. 3,577,406 and No. 3,767,640, for example), but they are not yet satisfactory because of insufficient activity against leukemia and other tumors, and/or undesirable side effects. Another class of nitrosourea derivatives is glycosyl derivatives of nitrosoureas which I have recently prepared and confirmed to be novel compounds, among which the most interesting compound is 1-(2-chloroethyl)-3-($\beta$-D-glucopyranosyl)-1-nitrosourea (abbreviated as GANU) which has a broad spectrum of antitumor activity against a variety of experimental tumors with shows good promise in its efficacy in human cancer chemotherapy (refer to T. Suami et al, U.S. Pat. No. 4,086,415).

BRIEF SUMMARY OF THE INVENTION

I have now found as a result of further investigations that certain specific novel nitrosourea derivatives, as hereinafter shown, exhibit a high inhibitory activity against transplanted leukemia and other tumors with a low toxicity as evidenced by in vivo tests.

According to one aspect of this invention, therefore, there are provided novel nitrosourea derivatives of the formula:

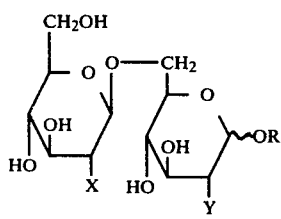
(I)

wherein one of X and Y represents a hydroxyl and another of them represents a group —NHCONNOCH$_2$CH$_2$Cl; R represents a hydrogen, alkyl or aryl; and ~ represents a single bond which may be the $\alpha$- or $\beta$ stereochemical configuaration.

DETAILED DESCRIPTION OF THE INVENTION

In the formula (I) representing the nitrosourea derivatives according to this invention, R may be a hydrogen atom or an alkyl or aryl group as defined above. Typically, the alkyl group may be methyl, ethyl, propyl, isopropyl, butyl, sec-butyl, t-butyl and i-butyl, and typical examples of the aryl group are phenyl and substituted phenyl such as chloro-substituted, nitro-substituted and methoxy-substituted phenyl.

The most typical nitrosourea derivatives according to this invention are:

Methyl 2'-[3-(2-chloroethyl)-3-(nitrosoureido)]-2'-deoxy-$\alpha$-gentiobioside;

Methyl 2'-[3'-(2-chloroethyl)-3-(nitrosoureido)]-2'-deoxy-$\beta$-gentiobioside;

Methyl 2-[3-(2-chloroethyl)-3-(nitrosoureido)]-2-deoxy-$\alpha$-gentiobioside;

Methyl 2-[3-(2-chloroethyl)-3-(nitrosoureido)]-2-deoxy-$\beta$-gentiobioside.

The novel nitrosourea derivatives according to this invention have shown that in vivo tests exhibit a high level of inhibitory activity against leukemia and other tumors. Anti-leukemic activity on Leukemia L 1210 of the most typical compound, methyl 2'-[3-(2-chloroethyl)-3-nitrosoureido]-2'-deoxy-$\alpha$-gentiobioside was tested as follows:

Animals

Male BDF$_1$ mice, aging about six weeks old and weighing 22±1 g were used in groups of five animals for each test.

Tumor cells

Leukemia L 1210 cells were inoculated intraperitoneally in a concentration of 1.36×10$^6$ cells/0.04 ml/mouse.

Administration of compound

The compound was dissolved in distilled water for injection to give a series of solutions in predetermined concentrations and 0.1 ml of each solution was administered intraperitoneally to each mouse once a day from the 24th hour after the tumor cell inoculation for 3 consecutive days. The antileukemic activity of the test compound was assessed by mean survival days, percentage increase in life-span, number of survivors after 60 days observation and the volume of ascites. The percentage increase in life-span (ILS) was calculated as follows:

$$ILS\ (\%) = T - C/C \times 100$$

T: The mean survival days of the treated animals
C: The mean survival days of the untreated animals
The test results are shown in the following table.

| Dose (mg/kg) | Mean survival days | ILS (%) | Volume of ascites (ml) | Number of survivors (after 60 days) |
|---|---|---|---|---|
| 32 | >40.8 | >466.7 | 0 | 3 |
| 16 | >24.6 | >241.7 | 0.3 | 1 |
| 8 | 14.0 | 94.4 | 1.1 | 0 |
| 4 | 11.6 | 61.4 | 0 | 0 |
| 2 | 8.6 | 19.4 | 0 | 0 |
| Control untreated) | 7.2 | — | 0.8 | 0 |

It will be clearly appreciated from the test results above that the novel nitrosourea derivatives according to this invention show a high value of ILS in a very low dose and are expected to be useful in human chemotherapy of leukemic and tumor diseases.

According to another aspect of this invention, therefore, there is provided a pharmaceutical composition comprising an effective amount of a nitrosourea compound of the formula (I) in association with a pharmaceutically acceptable excipient, carrier or diluent.

The pharmaceutical composition may be in a form known to suit the route of administration, that is, oral or injectable administration for man, injectable or intraperitoneal administration for animals. In general, therefore, the pharmaceutical composition may take such form as ampoule, capsule, tablet, powder, granule and the like to adapt for oral or injectable administration.

This invention also includes as a further aspect thereof a method for the therapeutic treatment of transplanted leukemic and tumor diseases in animals which comprises administering a therapeutically effective amount, at suitable intervals, of a nitrosourea compound of the formula (I) above. It will be appreciated that the amount to be actually applied of the nitrosourea compound will vary dependent upon the particular compound used, the particular composition formulated, the mode of application, the route of administration and others. Many factors which modify the action of the drug will be taken into account by the skilled in the art, for example, age, body weight, sex, diet, time of administration, route of administration, rate of metabolism or excretion, drug combination, sensitivities and severity or condition of the disease. Optimal application dose for a given set of conditions can be ascertained by the skilled in the art using conventional tests for the dosage determination in view of the above guidelines.

The novel nitrosourea compounds of the formula (I) according to this invention may be prepared simply by nitrosating the corresponding urea compounds in a manner known per se.

According to a still further aspect of this invention, therefore, there is provided a process for the preparation of nitrosourea derivatives of the formula (I) as defined above which comprises nitrosating a corresponding urea compound of the formula:

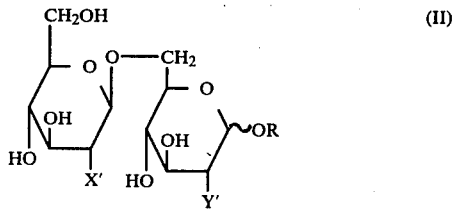

wherein one of X' and Y' represents a hydroxyl and another of them represents a group —NHCONHCH$_2$CH$_2$Cl and R and ~ have the same meanings as defined above with a nitrosating agent in a manner known per se.

In the process of this invention, the nitrosation reaction may be carried out in a manner known per se. Thus, as nitrosating agent, there may be used an alkali metal nitrite, nitrogen trioxide, dinitrogen tetroxide, nitrosyl chloride and the like as usual. As alkali metal nitrite, sodium or potassium nitrite is preferred. The nitrosation reaction may usually be conducted at a temperature of about $-10°$ C. to $30°$ C. in an inert reaction medium. As reaction medium, there may be used usual organic solvents such as acetone, methanol, ethyl acetate, ether, dioxane and tetrahydrofuran; organic acids such as formic and acetic acids; aqueous solutions of such organic acids; and aqueous solutions of inorganic acids such as hydrochloric acid. Under these conditions, the completion of the reaction may take about 1 to 12 hours.

After completion of the nitrosation reaction, the reaction mixture may, if necessary, be purified by recrystallization from a suitable solvent, or by treatment with an ion-exchange resin or the like to remove inorganic salts therefrom and by any other means known in the purification arts.

The following Examples will further illustrate the preparation of the novel nitrosourea derivatives according to this invention together with the preparation of the starting urea compounds.

EXAMPLE 1

Preparation of methyl 2'-[3-(2-chloroethyl)-3-nitrosoureido]-2'-deoxy-α-gentiobioside (Compound A)

(1) Methyl 2,3,3',4,4',6'-hexa-O-acetyl-2'-(benzyloxycarbonylamino)-2'-deoxy-α-gentiobioside (Compound 1)

3,4,6-Tri-O-acetyl-2-(benzyloxycarbonylamino)-2-deoxy-α-D-glucopyranosyl bromide (2.99 g) and methyl 2,3,4-tri-O-acetyl-α-D-glucopyranoside (1.66 g) are dissolved in dry benzene (35 ml), to which mercuric cyanide (2.7 g) and anhydrous calcium sulfate (3.5 g) are added. The mixture is refluxed for 2 hours and then stirred at room temperature for 19 hours. The resulting solution is filtered and the filtrate is diluted with chloroform (150 ml). The dilute solution is washed with a saturated sodium chloride solution, then with cold water repeatedly, dried with anhydrous sodium sulfate and concentrated in vacuo below $40°$ C. The residue is washed with ether and crystallized from ethanol to yield methyl 2,3,3',4,4',6'-hexa-O-acetyl-2'-(benzyloxycarbonylamino)-2'-deoxy-α-gentiobioside (Compound 1) as crystals. Yield 943 mg (26%). mp. $162°$–$163°$ C.; $[\alpha]_D^{25} + 68.7°$ (c 1.0, chloroform).

Elemental analysis: Found: C 53.29, H 5.96, N 1.99%. Calculated for $C_{33}H_{43}NO_{18}$: C 53.43, H 5.83, N 1.89%.

(2) Methyl 2'-(benzyloxycarbonylamino)-2'-deoxy-α-gentiobioside (Compound 2)

Compound 1 (195 mg) prepared in step (1) above is dissolved in an ammonia-saturated methanol solution (30 ml). The solution is allowed to stand at room temperatures overnight and then concentrated in vacuo. The residue is washed with ethyl acetate three times and crystallized from methanol to yield methyl 2'-(benzyloxycarbonylamino)-2'-deoxy-α-gentiobioside (Compound 2) as crystals. Yield 91 mg (72%). mp. $212°$–$214°$ C.; $[\alpha]_D^{25} + 37.6°$ (c 1.0, water).

Elemental Analysis: Found: C 51.32, H 6.30, N 2.83%. Calculated for $C_{21}H_{31}NO_{12}$: C 51.53, H 6.38, N 2.86%.

(3) Methyl 2'-methyl-2'-deoxy-α-gentiobioside (Compound 3)

Compound 2 (393 mg) prepared in step (2) above is dissolved in methanol (5 ml) and water (11 ml) and catalytically reduced with hydrogen (hydrogen pressure: 3.4 kg/cm$^2$) in the presence of a palladium black catalyst (200 mg). Thin layer chromatography (TLC) of the reaction mixture on silica gel using a solvent system of 5:8:10:7 (by volume) 28% ammonia-butanol-ethanol-water gives no spot at R$_f$0.68 for the starting compound but a new spot at R$_f$0.46. After removal of the catalyst by filtration, the filtrate is concentrated to give a product, methyl 2'-amino-2'-deoxy-α-gentiobioside (Compound 3) which is positive to the ninhydrin reaction. Yield 348 mg (99%).

(4) Methyl 2'-[3-(2-chloroethyl) ureido]-2'-deoxy-α-gentiobioside (Compound 4)

Compound 3 (348 mg) prepared in step (3) above is dissolved in methanol (5 ml) and 2-chloroethyl isocyanate (0.12 ml) is slowly added thereto with stirring under ice-cooling. The deposition of a white precipitate is observed. After the lapse of 30 minutes, the reaction mixture is allowed to stand at room temperature overnight. TLC of the resulting solution with a 5:8:10:7 (by volume) 28% ammonia-butanol-ethanol-water solvent system shows a single spot at $R_f$ 0.56. The solution is concentrated in vacuo below 30° C. and the residue is washed with ether to give a crude product (343 mg; yield 93%). Crystallization of the product from a 50% aqueous methanol (10 ml) affords crystals of methyl 2'-[3-(2-chloroethyl) ureido]-2'-deoxy-α-gentiobioside (Compound 4). Yield 172 mg (47%). mp. 196°–197° C. (decomposition); $[\alpha]_D^{20}+29.9°$ (c 0.6, water).

Elemental analysis: Found: C 41.74, H 6.21, N 5.88, Cl 7.49%. Calculated for $C_{16}H_{29}N_2ClO_{11}$: C 41.70, H 6.34, N 6.08, Cl 7.69%.

(5) Methyl 2'-[3-(2-chloroethyl)-3-nitrosoureido]-2'-deoxy-α-gentiobioside (Compound A)

Compound 4 (150 mg) prepared in step (4) above is suspended in acetone (3 ml) and nitrogen trioxide is injected into the suspension with stirring under ice-cooling. After a little while, the suspension is slowly changed into a solution with its color changing into deep blue. TLC of the resulting solution with a solvent system of 1:1 (by volume) chloroform-methanol shows a single spot at $R_f$ 0.64. The $R_f$ value of the starting compound is 0.33 with the same solvent system. After the lapse of about 30 minutes, the reaction solution is concentrated in vacuo at room temperature, to which n-hexane is added to give a precipitate. The precipitate is washed with isopropyl ether, affording 161 mg of crude product. Crystallization of the crude product from ethanol (0.5 ml) yields the object compound, methyl 2'-[3-(2-chloroethyl)-3-nitrosoureido]-2'-deoxy-α-gentiobioside (Compound A), as crystals. Yield 49 mg (31%). mp. 110°–112° C. (decomposition); $[\alpha]_D^{20}+32.9°$ (c 1.0, water).

Elemental analysis: Found: C 39.44, H 5.77, N 8.42, Cl 7.00%. Calculated for $C_{16}H_{28}N_3ClO_{12}$: C 39.21, H 5.76, N 8.58, Cl 7.24%.

EXAMPLE 2

Preparation of methyl 2'-[3-(2-chloroethyl)-3-nitrosoureido]-2'-deoxy-α-gentiobioside (Compound A)

Compound 4 (262 mg) prepared in Example 1 (4) is suspended in 99% formic acid (5 ml) and to the suspension is added sodium nitrite (60 mg) in small portions with stirring under ice-cooling. After continuing the stirring of the reaction mixture under ice-cooling for 1 hour, the mixture is diluted with the addition of water and then treated with 100 ml of a cation exchange resin "Amberlite" IR-120 (H+ form) (Amberlite is a trade name). The cation exchange resin is filtered off and the filtrate is concentrated in vacuo at room temperature to yield a pale yellow crystalline residue (266 mg) which is the object product, Compound A. Yield 98%. mp. 112°–113° C. (decomposition).

Elemental analysis: Found: C 39.33, H 5.70, N 8.54, Cl 7.14%. Calculated for $C_{16}H_{28}N_3ClO_{12}$: C 39.21, H 5.76, N 8.58, Cl 7.24%.

EXAMPLE 3

Preparation of methyl 2'-[3-(2-chloroethyl)-3-nitrosoureido]-2'-deoxy-β-gentiobioside (Compound B)

(1) Methyl 2,3,3',4,4',6'-hexa-O-acetyl-2'-benzyloxycarbonylamino-2'-deoxy-β-gentiobioside (Compound 5)

Methyl 2,3,4-tri-O-acetyl-β-D-glucopyranoside (2.04 g, 6.4 mmol) and mercuric cyanide (5.10 g, 20.0 mmol) are dissolved in dry benzene (100 ml), to which is then added anhydrous calcium sulfate (8.00 g), and the mixture is kept at 40° C. under anhydrous conditions with stirring. After 30 minutes, 3,4,6-tri-O-acetyl-2-(benzyloxycarbonylamino)-2-deoxy-α-D-glucopyranosyl bromide (10.04 g, 20.0 mmol) is added to the reaction mixture and the resulting mixture is heated under reflux for 3 hours. The reaction mixture is allowed to stand to room temperature and filtered to remove insoluble matter therefrom. Chloroform (150 ml) is added to the filtrate and the mixture is washed with saturated sodium chloride solution (150 ml×2) and then with water (150 ml×5). The mixture is dried with anhydrous sodium sulfate, filtered to remove the sodium sulfate and the filtrate is concentrated in vacuo to give a pale brown syrup. The syrup is crystallized from ethanol and recrystallized from ethanol, affording the titled compound (Compound 5) as white crystals. Yield 1.25 g (26.4%). mp. 182°–183° C.; $[\alpha]_D^{17}-6°$ (c 1.0, chloroform); $R_f$ 0.60 (5:2 (by volume) benzene-acetone).

Elemental Analysis: Found: C 53.42, H 5.76, N 1.86%. Calculated for $C_{33}H_{43}O_{18}N$: C 53.44, H 5.84, N 1.89%.

(2) Methyl 2'-(benzyloxycarbonylamino)-2'-deoxy-β-gentiobioside (Compound 6)

Compound 5 (620 mg, 0.82 mmol) prepared in step (1) above is dissolved in methanol saturated with ammonia (60 ml) and the solution is allowed to keep cold for 10 hours, after which time the completion of the deacetylation reaction is confirmed by TLC with a solvent system of 1:1 (by volume) chloroform-ethanol showing a single spot at $R_f$ 0.16. The resulting solution is concentrated in vacuo to yield a white solid residue. The residue is washed with ethyl acetate (2 ml×5) to remove the acetamide by-product, affording the deacetylation product (Compound 6) as a white solid. mp. 185.0°–187.5° C.

(3) Methyl 2'-amino-2'-deoxy-β-gentiobioside (Compound 7)

Compound 6 prepared in step (2) above is used in this step without purification. The compound is dissolved in a mixture of water (10 ml) and methanol (10 ml), to which palladium black (250 mg) is then added, and the mixture is reduced with hydrogen at a hydrogen pressure of 38 psi under stirring for 5 hours. TLC of the reaction mixture with a solvent system of 8:10:7:5 (by volume) n-butanol-ethanol-water-28% ammonia gives a single spot at $R_f$ 0.43 which is positive to ninhydrin reaction. The palladium black is filtered off and the filtrate is concentrated in vacuo to yield the reduction product (Compound 7) as a syrupy residue.

(4) Methyl 2'-[3-(2-chloroethyl) ureido]-2'-deoxy-β-gentiobioside (Compound 8)

Compound 7 prepared in step (3) above is used in this step without purification. Thus, it is dissolved in methanol (5 ml) and to the solution 2-chloroethyl isocyanate (0.25 ml, 1.37 mmol) is slowly added dropwise with stirring under ice-cooling. Immediately, white crystals are deposited, so that the stirring cannot be contained. Then, the whole mixture is allowed to kept cold for further 12 hours and is concentrated in vacuo to yield a white solid residue. The residue is crystallized from a mixture of water (5 ml) and methanol (5 ml), affording the titled compound (Compound 8) as white needles. Yield 126 mg (33.3% based on the Compound 5). mp. 174°–176° C. (decomposition); $[\alpha]_D^{19} -40°$ (c 1.0, water); $R_f$ value 0.55 (8:10:7:5 (by volume) n-butanol-ethanol-water-28% ammonia); IR spectrum; 1625 cm$^{-1}$, 1575 cm$^{-1}$.

Elemental analysis: Found: C 41.44, H 6.25, N 5.81, Cl 7.51% Calculated for $C_{16}H_{29}O_{11}N_2Cl$: C 41.70, H 6.34, N 6.08, Cl 7.69%.

(5) Methyl 2'-[3-(2-chloroethyl)-3nitrosoureido]-2'-deoxy-$\beta$-gentibioside (Compound B)

The Compound 8 (100 mg, 0.217 mmol) prepared in step (4) above is suspended in acetone (3 ml) and the suspension is ice-cooled, into which nitrogen trioxide gas is injected for 40 minutes. During the injection, the reaction mixture changes from a white turbid appearance to a transparent deep bluish green appearance. The mixture is concentrated in vacuo with expulsion of the dissolved nitrogen trioxide, wherever the color of the concentrate becomes pale yellow. The acetone is distilled off and the residue is washed with n-hexane (5 ml×2). Upon adding isopropyl ether (3 ml) to the residue, a pale yellowish white precipitate is formed and separated by centrifugation to remove the supernatant liquid. To the latter liquid is added a fresh portion (3 ml) of isopropyl ether and the same operation as above is repeated. The collected pale yellowish white precipitates are sucked by a vacuum pump to remove the solvent, affording a pale yellow solid, which is the object product, Compound B. Yield 43 mg (40%). $R_f$ value 0.78 (1:1 (by volume) acetone-methanol); UV absorption spectrum: 2537 Å; IR spectrum: 1,700 (>C=O), 1,530 (—N—H), 1490 cm$^{-1}$ (—N=O).

Elemental analysis: Found: C 39.01, H 6.22, N 8.33, Cl 7.18%. Calculated for $C_{16}H_{28}O_{12}N_3Cl$: C 39.21, H 5.99, N 8.53, Cl 7.24%.

EXAMPLE 4

Preparation of methyl 2-[3-(2-chloroethyl)-3-nitrosoureido]-2-deoxy-$\alpha$-gentiobioside (Compound C)

(1) Methyl 2',3,3',4,4',6'-hexa-O-acetyl-2-(benzyloxycarbonylamino)-2-deoxy-$\alpha$-gentiobioside (Compound 9)

Mercuric cyanide (6.0 g, 23.7 mmol) and anhydrous calcium sulfate (12 g) are added to dry benzene (120 ml) and the mixture is heated on an oil bath to 40° C. To the mixture are then added methyl 3,4-di-O-acetyl-2-(benzyloxycarbonylamino)-2-deoxy-$\alpha$-D-glucopyranoside (3.4 g, 9.6 mmol) and 2,3,4,6-tetra-O-acetyl-$\alpha$-D-glucopyranosyl bromide (7.5 g, 17.4 mmol). The mixture is heated up to 80° C., at which the reaction is conducted for 1 hour, and allowed to cool to a temperature of 45° C. Then, mercuric cyanide (6.0 g, 23.7 mmol) and 2,3,4,6-tetra-O-acetyl-$\alpha$-D-glucopyranosyl bromide (7.5 g, 17.4 mmol) are added to the mixture and the whole mixture is heated under reflux overnight. At this point, the formation of the titled compound as a condensation product is confirmed by TLC using a solvent system of 5:1 (by volume) benzene-acetone. The reaction mixture is diluted with chloroform (180 ml), washed with a saturated sodium chloride solution twice, then with water four times, dehydrated with anhydrous sodium sulfate for 1 hour and concentrated in vacuo to obtain the titled compound (Compound 9) as a pale yellow syrup. The compound is used for the subsequent deacetylation step without purification.

(2) Methyl 2-(benzyloxycarbonylamino)-2-deoxy-$\alpha$-gentiobioside (Compound 10)

Compound 9 in the form of a syrup obtained in step (1) above is dissolved in methanol (60 ml), to which 0.1 N methanolic sodium methoxide solution (6 ml) is then added with stirring under ice-cooling. The mixture is allowed to stand at room temperature for 1 hour for completing the reaction. At this point, TLC of the reaction mixture using a solvent system of 1:1 (by volume) chloroform-ethanol shows no spot for the starting compound but a main spot at $R_f$0.45. The mixture is neutralized with a cation exchange resin "Amberlite" IR-120 (B), H$^+$ form, (Amberlite is a trade name). The resin is filtered off and the filtrate is concentrated in vacuo, crystallized from a mixed solvent of methanol-ether and finally recrystallized from a mixture of methanol-water to yield the titled compound (Compound 10). Yield 890 mg, 1.82 mmol; 21.2% calculated on the starting methyl 3,4-di-O-acetyl-2-(benzyloxycarbonylamino)-2-deoxy-$\alpha$-D-glucopyranoside. mp. 235°–236° C.; $[\alpha]_D^{22} +50.9°$ (c 1.0, water).

Elemental analysis: Found: C 51.788, H 6.41, N 2.75%. Calculated for $C_{21}H_{31}NO_{12}$: C 51.53, H 6.38, N 2.86%.

(3) Methyl 2-[3-(2-chloroethyl)ureido]-2-deoxy-$\alpha$-gentiobioside (Compound 11)

Palladium black (200 mg) is suspended in water (5 ml) and the suspension is shaken under a hydrogen pressure of 40 psi. for 30 minutes to give a hydrogen-saturated state.

Compound 10 (850 mg, 1.73 mmol) prepared in the step (2) above is dissolved in a solvent mixture of 1:1 (by volume) water-methanol and the resulting solution is added to the hydrogen-saturated suspension. The catalytic reduction is conducted under a hydrogen pressure of 40 psi. for 2.5 hours. At this point, TLC of the reaction mixture using a solvent system of 4:5:2:4 (by volume) n-butanol-ethanol-water-17% ammonia shows no spot of Compound 10 but a new spot at $R_f$0.5 which is positive to the ninhydrin reaction. The palladium black is filtered off and the filtrate is concentrated in vacuo to yield a transparent syrupy residue.

The residue is dissolved in methanol (15 ml) and 2-chloroethyl isocyanate (0.2 ml, 2.41 mmol) is added dropwise to the methanolic solution with stirring under ice-cooling. The mixture is stirred at room temperature overnight, during which the whole is changed into a white gel. The gel is dissolved in a small amount of a mixture of water and ethanol and the solution, which shows a single spot at $R_f$0.6 which is negative to ninhydrin reaction in TLC using a solvent system of 4:5:2:4 (by volume) n-butanol-ethanol-water-17% ammonia, is concentrated in vacuo to yield crystals which are washed with a solvent mixture of 1:1 (by volume) ethanol-ethyl acetate (30 ml×2) to afford the titled compound, Compound 11. Yield 620 mg, 1.35 mmol; 72% calculated on Compound 10. mp. 151.0°–151.5° C. (decomposition); $[\alpha]_D^{20} +54.2°$ (c 1.0, water).

Elemental analysis: Found: C 41.74; H 6.21, N 5.88, Cl 7.49%. Calculated for $C_{16}H_{29}N_2O_{11}Cl$: C 41.70, H 6.34, N 6.08, Cl 7.69%.

(4) Methyl 2-[3-(2-chloroethyl)-3-nitrosoureido]-2-deoxy-α-gentiobioside (Compound C)

Compound 11 (200 mg, 0.4 mmol) prepared in step (3) above is suspended in acetone (5 ml) and nitrogen trioxide is injected into the suspension for 3 minutes under ice-cooling, during which the reaction mixture becomes a transparent liquid dark blue and shows in TLC, using a solvent system of 1:1 (by volume) chloroform-methanol, spots of both the starting and object compounds at $R_f$ 0.6 and $R_f$ 0.4, respectively. After 1 hour, the reaction mixture becomes discolored into yellowish green, without the spot at $R_f$ 0.6 of the starting compound and with the single spot at $R_f$ 0.4 in TLC of the same solvent system as above. The mixture is concentrated in vacuo and the resulting syrupy residue is washed with n-hexane and crystallized from isopropylether, affording the titled compound, Compound C, with a yield of 159 mg, 0.32 mmol (73%). mp. 67°–68° C. (decomposition); $[\alpha]_D^{22} + 39.4°$ (c 10, water).

Elemental analysis: Found: C 39.21, H 5.99, N 8.58, Cl 7.24%. Calculated for $C_{16}H_{28}N_3O_{12}Cl$: C 38.97, H 5.77, N 8.92, Cl 6.92%.

EXAMPLE 5

Preparation of methyl 2-[3-(2-chloroethyl)-3-nitrosoureido]-2-deoxy-β-gentiobioside (Compound D)

(1) Methyl 2′,3,3′,4,4′,6′-hexa-O-acetyl-2-(benzyloxycarbonylamino)-2-deoxy-β-gentiobioside (Compound 12)

Methyl 3,4-di-O-acetyl-2-(benzyloxycarbonyl amino)-2-deoxy-β-D-glucopyranoside (710 mg, 1.67 mmol) is dissolved in dry benzene (40 ml) and then mercuric cyanide (3.0 g, 6.2 mmol) and anhydrous calcium sulfate (5.0 g) are added thereto and the mixture is heated under stirring at 50° C. for 30 minutes. Then, 2,3,4,6-tetra-O-acetyl-α-D-glucopyranosyl bromide (2.6 g, 6.1 mmol) is added and the mixture is heated at 70° C. overnight to complete the reaction. The reaction mixture is allowed to cool to room temperature and then filtered. The residue is washed with chloroform (60 ml) and the washings are combined with the filtrate. The combined chloroform-benzene solution is washed with saturated sodium chloride solution (150 ml×2), then with water (50 ml×4), dried with anhydrous sodium sulfate and concentrated in vacuo to give a syrup. Ethanol (30 ml) is added to the syrup and the mixture is heated to form a solution and is allowed to stand in a refrigerator overnight. Supernatant ethanol is removed by decantation to obtain a syrupy residue containing crystals partially deposited. The residue is purified by silica gel-chromatography (C-200, 100 ml) using a solvent system of 10:1 (by volume) benzeneacetone as eluent, affording the titled compound, Compound 12, as crystals. Yield 340 mg (27.0%). mp. 189°–190.5° C.; $[\alpha]_D^{20} - 3°$ (c 1.0, $CHCl_3$).

(2) Methyl 2-(benzyloxycarbonylamino)-2-deoxy-β-gentiobioside (Compound 13)

Compound 12 (340 mg, 0.45 mmol) prepared in step (1) above is dissolved in ammonia-saturated methanol (20 ml) and is allowed to stand overnight under ice-cooling. At this point, TLC of the reaction mixture confirms disappearing of the spot of the starting compound. The reaction mixture is concentrated in vacuo, washed with ethyl acetate (10 ml×2) and crystallized from methanol to obtain the titled compound, Compound 13, as white crystals. Yield 180 mg (79.3%). mp. 225°–227° C.

(3) Methyl 2-[3-(2-chloroethyl) ureido]-2-deoxy-β-gentiobioside (Compound 14)

Compound 13 (170 mg) prepared in step (2) above is dissolved in a mixed solvent (10 ml) of 1:1 (by volume) water-methanol, to which is then added activated palladium black (100 mg) and the catalytic reduction is conducted at a hydrogen pressure of 40 psi. at room temperatures for 2 hours. After the palladium black is filtered off, the filtrate is concentrated in vacuo to yield a syrupy residue. TLC of the residue using a solvent system of 4:5:2:4 (by volume) n-butanol-ethanol-water-17% ammonia shows a single spot at $R_f$ 0.55 which is positive to the ninhydrin reaction.

The syrupy residue, without purification, is dissolved in methanol (5 ml), to which 2-chloroethyl isocyanate (0.2 ml, 2.41 mmol) is added dropwise under ice-cooling and the reaction mixture is kept overnight for the completion of reaction to give a white gel. The mixture is then concentrated to dryness in vacuo and methanol (10 ml) is added to the residue. The mixture is heated to dissolve as much of the residue as possible, cooled and filtered to obtain the titled compound, Compound 14, which shows a spot at $R_f$ 0.65 in TLC using a solvent system of 4:5:2:4 (by volume) n-butanol-ethanol-water-17% ammonia. Yield 107 mg (68.8%). mp. 152°–153° C. (decomposition).

(4) Methyl 2-[3-(2-chloroethyl)-3-nitrosoureido]-2-deoxy-β-gentiobioside (Compound D)

Compound 14 (100 mg, 0.217 mmol) prepared in step (3) above is suspended in acetone (3 ml) and ice-cooled, into which $N_2O_3$ gas is then injected for 5 minutes. The reaction is conducted for 1 hour under ice-cooling. The reaction mixture is concentrated in vacuo and washed with n-hexane (5 ml×2). Isopropylether (5 ml) is added to the concentrate to obtain the object product, Compound D, as a pale yellowish white powder. Yield 83 mg (77.6%). mp. 67° C. (decomposition); $[\alpha]_D^{24} - 27.4°$ (c 0.5, $H_2O$).

What I claim is:

1. Notrosourea derivarives of the formula:

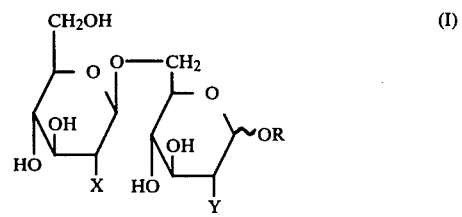

(I)

wherein when X=OH, Y=NHCONNOCH$_2$CH$_2$Cl and when Y=OH, X=NHCONNOCH$_2$CH$_2$Cl; R represents a hydrogen lower alkyl, phenyl or substituted phenyl; and ~ represents a single bond which may be in the α- or β-stereochemical configuration.

2. Methyl 2′-[3-(2-chloroethyl)-3-nitrosoureido]2′-deoxy-α-gentiobioside.

3. Methyl 2′-[3-(2-chloroethyl)-3-nitrosoureido]2′-deoxy-β-gentiobioside.

4. Methyl 2-[3-(2-chloroethyl)-3-nitrosoureido]2-deoxy-α-gentiobioside.

5. Methyl 2-[3-(2-chloroethyl)-3-nitrosoureido]2-deoxy-β-gentiobioside.

6. A pharmaceutical composition effective against transplanted leukemia or tumors, comprising a safe and effective amount of a compound according to claim 1 in combination with a pharmaceutically acceptable carrier.

7. A method for inhibiting the growth of transplanted leukemia or tumors, which comprises administering a safe an effective amount of a compound according to claim 1 to an animal afflicted therewith.

* * * * *

UNITED STATES PATENT AND TRADEMARK OFFICE
CERTIFICATE OF CORRECTION

PATENT NO. : 4,251,515
DATED : February 17, 1981
INVENTOR(S) : Tetsuo Suami

It is certified that error appears in the above–identified patent and that said Letters Patent are hereby corrected as shown below:

Column 10, line 44, "Notrosourea" should be "Nitrosourea"

Column 10, line 58, after "hydrogen" insert ","

Signed and Sealed this

Ninth Day of June 1981

[SEAL]

Attest:

RENE D. TEGTMEYER

Attesting Officer

Acting Commissioner of Patents and Trademarks